United States Patent [19]

Mamalis et al.

[11] 3,968,220

[45] July 6, 1976

[54] IMIDAZOLE INSECTICIDES
[75] Inventors: Patrick Mamalis, Reigate; Eric Arthur Stuart La Croix, Dorking; Solomon Ezekiel Mhasalker, Worcester Park, all of England
[73] Assignee: Beecham Group Limited, Great Britain
[22] Filed: Sept. 5, 1974
[21] Appl. No.: 503,367

Related U.S. Application Data
[62] Division of Ser. No. 301,677, Oct. 27, 1972, Pat. No. 3,850,953.

[30] Foreign Application Priority Data
Nov. 13, 1971 United Kingdom............... 52810/71
Nov. 13, 1971 United Kingdom............... 52811/71

[52] U.S. Cl............................... 424/273; 424/200; 424/263; 424/267; 424/270
[51] Int. Cl.²........................................... A01N 9/22

[58] Field of Search................. 424/273; 260/309.2, 260/309

[56] References Cited
UNITED STATES PATENTS
3,696,116  10/1972  Jeanmart et al. .................... 260/309

OTHER PUBLICATIONS
Chem. Abstracts, vol. 75, (1972), p. 5813a.
Chem. Abstracts, vol. 74, (1971), p. 3556z.
Chem. Abstracts, vol. 63, (1915), p. 5629.
Chem. Abstracts, vol. 67, (1967), p. 54123u.

Primary Examiner—V. D. Turner

[57] ABSTRACT
Method for insect control and insecticidal compositions containing substituted imidazoles as the active insecticidal agents for agricultural and horticultural use.

29 Claims, No Drawings

IMIDAZOLE INSECTICIDES

This application is a division of application Ser. No. 301,677 filed Oct. 27, 1972, now U.S. Pat. No. 3,850,953, granted Nov. 26, 1974.

This invention relates to novel hydroxy imidazole derivatives, to methods of their preparation and to pesticidal compositions containing them.

We have found that a novel group of hydroxy imidazole derivatives have marked pesticidal activity, individual compounds with the group have insecticidal activity and more particularly aphicidal activity while being substantially free of herbicidal activity. It will be appreciated that this combination of effects render the compounds useful in agriculture and horticulture.

Accordingly the present invention provides a pesticidal composition comprising a compound of general formula:

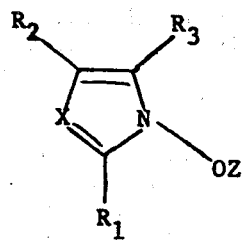

wherein $R_1$ is a hydrogen atom, an optionally substituted aromatic, heteroaromatic, straight- or branched-chain saturated or unsaturated $C_1$–$C_{12}$ aliphatic or araliphatic hydrocarbon group, $R_2$ and $R_3$ are the same or different and each is hydrogen atom or an optionally substituted aryl or $C_1$–$C_{12}$ aliphatic group or a carboxylic ester.

The group X is N or N → O and Z is a hydrogen atom or a group $CO.N.R_4R_5$ wherein $R_4$ is a hydrogen atom, an aryl or an optionally substituted lower aliphatic group or araliphatic or acyl group. $R_5$ is a hydrogen atom, an aryl or lower aliphatic group or $R_4$ and $R_5$ together with the nitrogen atom to which they are attached form a heterocyclic group- or salts thereof; together with one or more conventionally used diluents, excipients or dispersants.

The term "lower" as used herein means that the group contains 1 to 6 carbon atoms.

The term "heteroaromatic" as used herein is intended to include heterocyclic groups which are aromatic in character.

Suitable groups $R_1$ include the hydrogen atom, the methyl, ethyl, allyl, propyl, butyl, furyl, thienyl, pyridyl, thiazolyl and pyrryl groups, unsubstituted phenyl or naphthyl groups or such phenyl or naphthyl groups substituted with one or more halogen atoms, lower alkyl or lower alkoxyl groups, or lower alkyl groups substituted by a phenyl group.

Preferred groups $R_1$ include the methyl, ethyl, allyl, n-propyl, isopropyl, n-butyl, iso-butyl, t-butyl, sec-butyl and benzyl groups.

Suitable values for $R_2$ and $R_3$ include the hydrogen atom, the methyl, ethyl, propyl, butyl or phenyl group.

Suitable groups $R_4$ include the hydrogen atom, methyl, ethyl, propyl, butyl, benzyl and phenyl formyl, acetyl, propionyl, chloroacetyl or benzoyl groups; suitable groups $R_5$ include the methyl, ethyl, propyl, butyl or phenyl groups; or $R_4$ and $R_5$ together with the nitrogen to which they are attached form a 5- or 6-membered heterocyclic group.

Preferred groups $R_4$ or $R_5$ include the methyl, ethyl, and phenyl groups or together with the nitrogen atom to which they are attached form a N-piperidino or N-pyrrolidyl group.

A particularly preferred group $R_4$ is the methyl group. Thus a preferred value for the $CO-NR_4R_5$ moiety is $CO-N(CH_3)_2$.

Suitable salts include any conventional acid addition salt formed by an organic or inorganic acid. Thus sulphates, nitrates, phosphates, hydrohalides, acetates, formates and the like are all included within the scope of the invention.

Compounds for use in the compositions of the present invention include the following:

2,4,5-Trimethyl-1-hydroxyimidazole;
4,5-Dimethyl-2-ethyl-1-hydroxyimidazole
4,5-Dimethyl-1-hydroxy-2-n-propylimidazole;
4,5-Dimethyl-1-hydroxy-2-isopropylimidazole;
4,5-Dimethyl-2-n-butyl-1-hydroxyimidazole;
4,5-Dimethyl-1-hydroxy-2-isobutylimidazole;
4,5-Dimethyl-1-hydroxy-2-phenylimidazole;
4,5-Dimethyl-2-benzyl-1-hydroxyimidazole;
4,5-Dimethyl-1-hydroxy-2-nitrophenylimidazole;
4,5-Dimethyl-1-hydroxy-2-(4-isopropylphenyl) imidazole;
4,5-Dimethyl-2-furyl-1-hydroxyimidazole;
4,5-Diphenyl-1-hydroxy-2-isopropylimidazole;
4,5-Diphenyl-1-hydroxy-2-isobutylimidazole;
2,4,5-Triphenyl-1-hydroxyimidazole;
4,5-Dimethyl-1-hydroxy-2-(4'-fluorophenyl) imidazole;
4,5-Dimethyl-1-hydroxy-2-(4'hydroxy-3'-methoxyphenyl)imidazole;
4,5-Dimethyl-1-hydroxy-2-(3',4'-methylenedioxyphenyl)imidazole;
4,5-Dimethyl-1-hydroxy-2-(3',4'-dichlorophenyl) imidazole;
4-Methyl-5-ethyl-1-hydroxy-2-n-propylimidazole;
4-Methyl-5-ethyl-1-hydroxy-2-isopropyl imidazole;
4-Ethyl-5-methyl-1-hydroxy-2-n-propyl imidazole;
4-Ethyl-5-methyl-1-hydroxy-2-isopropyl imidazole;
4-Methyl-5-isopropyl-1-hydroxy-2-n-propyl imidazole;
4-Methyl-2,5-di-isopropyl-1-hydroxyimidazole;
4-Methyl-5-ethyl-1-hydroxy-2-n-propylimidazole-3-oxide;
4-Methyl-5-ethyl-1-hydroxy-2-isopropylimidazole-3-oxide;
4-Methyl-2,5-di-isopropyl-1-hydroxyimidazole-3-oxide;
4-Methyl-5-ethyl-1-hydroxy-2-phenylimidazole-3-oxide;
1-Hydroxy-2-ethyl-4-methyl-5-carbethoxyimidazole;
1-Hydroxy-2-n-propyl-4-methyl-5-carbethoxyimidazole;
1-Hydroxy-2-iso-propyl-4-methyl-5-carbethoxyimidazole;
1-Hydroxy-2-n-propyl-4-methyl-5-carbomethoxyimidazole;
1-Hydroxy-2-iso-propyl-4-methyl-5-carbomethoxyimidazole;
4,5-Dimethyl-1-hydroxy-2-methylimidazole-3-oxide;
4,5-Dimethyl-1-hydroxy-2-ethylimidazole-3-oxide;
4,5-Dimethyl-1-hydroxy-2-n-propylimidazole-3-oxide;
4,5-Dimethyl-1-hydroxy-2-isopropylimidazole-3-oxide;

4,5-Dimethyl-1-hydroxy-2-n-butylimidazole-3-oxide;
4,5-Dimethyl-1-hydroxy-2-isobutylimidazole-3-oxide;
4,5-Dimethyl-1-hydroxy-2-n-pentylimidazole-3-oxide;
4,5-Dimethyl-1-hydroxy-2-nonylimidazole-3-oxide;
4,5,Dimethyl-1-hydroxy-2-phenylimidazole-3-oxide;
4,5-Dimethyl-2-ethylimidazole-1-methylcarbamate;
4,5-Dimethyl-2-isopropylimidazole-1-methyl-carbamate
4,5-Dimethyl-2-isobutylimidazole-1-methyl-carbamate;
4,5-Dimethyl-2-phenylimidazole-1-methyl-carbamate;
4,5-Dimethyl-2-isopropylphenylimidazole-1-methyl-carbamate;
4,5-Dimethyl-2-(2-furyl)imidazole-1-methylcarbamate;
4,5-Dimethyl-2-ethylimidazolo-1-ethylcarbamate;
4,5-Dimethyl-2-phenylimidazole-1-ethylcarbamate;
4,5-Dimethyl-2-ethylimidazole-
4,5-Dimethyl-2-(2-furyl)imidazole-1-phenyl carbamate;
4,5-Dimethyl-2-methylimidazole-1-dimethylcarbamate;
4,5-Dimethyl-2-ethylimidazole-1-dimethylcarbamate;
4,5-Dimethyl-2-n-propylimidazole-1-dimethylcarbamate;
4,5-Dimethyl-2-isopropylimidazole-1-dimethylcarbamate;
4-Methyl-2,5-diethylimidazole-1-dimethylcarbamate;
4-Methyl-5-ethyl-2-n-propylimidazole-1-dimethylcarbamate;
4-Methyl-5-ethyl-2-isopropylimidazole-1-dimethylcarbamate;
4-Methyl-5-isopropyl-2-n-propylimidazole-1-dimethylcarbamate;
4-Methyl-2,5-di-isopropylimidazole-1-dimethylcarbamate;
4-Ethyl-5-methyl-2-n-propylimidazole-1-dimethylcarbamate;
4-Ethyl-5-methyl-2-isopropylimidazole-1-dimethylcarbamate;
1-N,N-dimethylcarbamoxy-2-isopropyl-4-methyl-5-carbethoxyimidazole;
1-N,N-dimethylcarbamoxy-2-n-propyl-4-methyl-5-carbmethoxyimidazole;
1N,N-dimethylcarbamoxy-2-isopropyl-4-methyl-5-carbomethoxyimidazole;
1-N,N-dimethylcarbamoyloxy-4-methyl-ethyl-2-isopropylimidazole-3-oxide;
4,5-Dimethyl-2-n-butylimidazole-1-dimethylcarbamate;
4,5-Dimethyl-2-isobutylimidazole-1-dimethylcarbamate;
4,5-Dimethyl-2-phenylimidazole-1-dimethylcarbamate;
4,5-Dimethyl-2-benzylimidazole-1-dimethylcarbamate;
4,5-Dimethyl-2-isopropylimidazole-1-diethylcarbamate;
4,5-Dimethyl-2-isobutylimidazole-1-diethylcarbamate;

Compounds within general formula (I) have shown contact insecticidal activity and also have been shown to possess systemic insecticidal activity -by which herein is meant that if the compound is applied to a plant and in particular to the locus of the roots of a plant, then the compound is transported through the plant to a sufficient extent that any insects feeding on the plant will be subjected to the insecticidal activity of that compound.

The systemic activity of compounds of the invention is particularly good when $R_1 = R_2 = CH_3$ and $Z = CO.N.R_4R_5$. Such compounds are particularly effective against leaf feeding insects, especially Hemiptera, and in particular aphids. The compounds of the invention also show repellency and/or anti-feeding activity.

The compositions according to the invention can be formulated for use in any desired way. Generally such formulations include the compound in association with a suitable carrier or diluent. Such carriers may be liquid or solid and designed to aid the application of the compound either by way of dispersing it where it is to be applied or to provide a formulation which can be made up by the user into a dispersable preparation.

Liquid preparations thus may include preparations of the compound in the form of solutions or emulsions which may be used on their own or may be adapted to be made up with water or other diluents to form sprays and the like. In those cases where the pesticide is to be applied to a plant the liquid carrier should be one that is non-phytotoxic under the conditions of use. Generally, such preparations will include a wetting, dispersing or emulsifying agent. Other liquid preparations include aerosols, in which the compound is associated with a liquid carrier or propellant.

Other preparations include dusts and wettable powders, granules and pellets and semi-solid preparations such as pastes. Such preparations may include inert solids or liquid diluents such as clays which may themselves have wetting properties, and/or wetting, dispersing or emulsifying agents; binding and/or adhesive agents may also be included. Solid preparations also include thermal fumigating mixtures wherein the compound is associated with a solid to promote vaporisation.

In general any carrier diluent or like agent used should be non-toxic to humans and other mammals and to plants.

Certain of the compounds included in general formula (I) are novel. Thus in a second aspect the invention provides compounds of general formula (II)

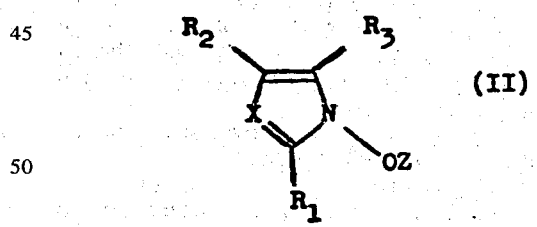

wherein $R_1$ is a hydrogen atom, an optionally substituted aromatic, heteroaromatic, straight- or branched-chain saturated or unsaturated $C_1-C_{12}$ aliphatic or araliphatic hydrocarbon group, $R_2$ and $R_3$ are the same or different and each is hydrogen or an optionally substituted aryl or $C_1-C_{12}$ aliphatic group or a carboxylic ester group, X is N or N → O and Z is a hydrogen atom or a group $CO.N.R_4R_5$ wherein $R_4$ is a hydrogen atom, an aryl or optionally substituted lower aliphatic group or araliphatic or acyl group $R_5$ is a hydrogen atom, an aryl or lower aliphatic group or $R_4$ and $R_5$ together with the nitrogen atom to which they are attached form a heterocyclic group; or salts thereof except that a. when Z is H, X is N, and $R_2$ and $R_3$ are both methyl groups, $R_1$ must not be a methyl, methoxymethyl, trichloromethyl, ethyl, isopropyl, vinyl, 1-methyl-n-butyl, 1-ethyl-n-butyl, or phenyl and b. when Z is H, X is N, and $R_2$ and $R_3$ are both phenyl groups, $R_1$ must not be phenyl, methyl, vinyl, or 2-ethyl-n-pentyl and c. when Z is H, X is N → O and $R_2$ and $R_3$ are both methyl, $R_1$ must not be methyl, ethyl, phenyl, 4-tolyl, 4-methoxyphenyl, 2-nitrophenyl or 3,4-methylenedioxyphenyl and d. when X is N, $R_1$ is phenyl, $R_2$ and $R_3$ are both $CH_3$, then Z must not be a group —CO.NHPh or —CO.NH.$C_2H_5$.

Suitable and preferred groups $R_1$, $R_2$, $R_3$, $R_4$ and $R_5$ are as described for the compounds of formula I.

In a third aspect the invention provides a process for the preparation of compounds of general formula (II) wherein Z=H which process comprises reacting a diketone monoxime of general formula (III):

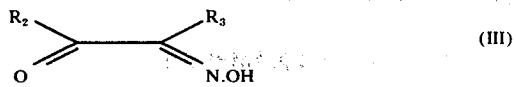

(wherein $R_2$ and $R_3$ are as defined with reference to formula (II) above) either (i) with ammonia and an an aldehyde of general formula (IV):

(wherein $R_1$ is as defined with reference to formula (II) above to form compounds of formula (II) wherein X=N and Z=H, or (ii) with an aldoxime of general formula (V):

(wherein $R_1$ is as defined with reference to formula (II) above) to form compounds of formula (II) wherein X = N → O and Z = H.

For the preparation of compounds (II) wherein X = N and Z = H, the reaction may conveniently be carried out in a water miscible solution as this allows the ammonia to be added in aqueous solution to a mixture of compounds (III) and (IV). Suitable solvents include ethers such as dioxane, tetrohydrofuran and the like and alcohols such as methanol or ethanol of the like. Solvent volumes are preferably kept low.

The reaction temperature is generally kept below 80°C preferably below 60° in order to minimise side reactions. As the reaction is often exothermic this may involve cooling the reaction mixture.

For the preparation of compounds (II) wherein X = N → O and Z = H the reaction may be carried out over a wide range of temperatures, for example, from 0° to 100°C. It is general, however, to warm the reaction mixture for some time to bring the reaction to completion.

In a further aspect this invention provides a process for the preparation of a compound (II) wherein Z = CO.N$R_4R_5$ (wherein $R_4$ and $R_5$ are as defined with reference to formula (II) above) which process comprises reacting a compound of general formula (VI):

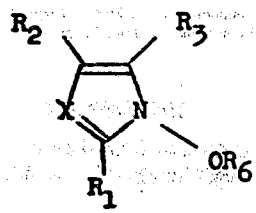

(VI)a $R_6$ = H or a cation
(VI)b $R_6$ = COCl or COBr.

(wherein $R_1$, $R_2$ and $R_3$ are as defined with reference to formula (II) above) with a carbamoylating agent which is either (i) a compound of formula $R_4R_5$NH (wherein $R_4$ and $R_5$ are as defined with reference to formula (II) above) when (VI) is (VIb); or (ii) a compound of formula $R_5$NCO or $R_4R_5$N.COY when (VI) is (VIa) (wherein Y is a group readily displaced by the optionally salted hydroxyl group) and then if desired replacing one group $R_4$ or $R_5$ by methods known per se.

Suitable values for Y include bromine, chlorine, methanesulphonyl, p-toluenesulphonyl and the like, chlorine being preferred.

The compounds (VIb) may be prepared from compounds of general formula (VIa) by reaction with $COCl_2$ or $COBr_2$ in a inert solvent. Generally such a reaction will take place in an inert aprotic solvent at an ambient or low temperature, preferably in the range −10° to +30°C.

The conversion of a compound (VIb) into a compound of the invention may take place in an aprotic solvent such as a halogenated hydrocarbon such as chloroform, methylene chloride and the like, a ketone solvent such as acetone, methyl ethyl ketone and the like or an ether solvent such as tetrahydrofuran, dioxane or the like.

The reaction may take place at low, ambient or elevated temperature a temperature range of −10°C to +150°C being suitable, 0° to 80°C being preferred.

In general, for this process, it is preferable that $R_4$ is not a hydrogen atom or an acyl group. Preferably $R_4$ and $R_5$ are both alkyl groups, most preferably both methyl groups.

When $R_4$ is H or an aliphatic or aryl group, a suitable manner of preparation of a compound (II) is by the reaction of a compound (VIa) with a carbamoylating agent of the formula $R_5$NCO preferably in an inert solvent such as a ketone solvent such as acetone or methyl ethyl ketone at an ambient or elevated temperature.

When $R_4$ and $R_5$ are both aliphatic or aryl groups, a preferred carbamoylating agent to react with a compound (VIa) is a compound of the formula $R_4R_5N.CO.Y$ in an aprotic solvent at low ambient or elevated temperature. Preferably $R_6$ = Na or when $R_6$ = H a base, such as sodium carbonate, may be added.

Compounds (II) of the invention in which $R_4$ is H may be converted into compounds (II) in which $R_4$ is an aliphatic, araliphatic or acyl group by known methods. For example, a compound in which $R_4$ is an alkyl group may be prepared from the corresponding $R_4$ = H compound by reacting the lithium butyl or the like to form the ion and then reacting this with an alkyl halide or the like; a compound in which $R_4$ is an acyl group may be prepared from the corresponding $R_4$ = H compounds by standard methods of acylation such as the reaction with an acid halide or anhydride in conventional manner.

The present invention also provides a method for the control of insects which comprises the application to the insect or its habitat of a compound of formula I above. Preferably the said compound is topically applied to a plant.

The preparation and insecticidal properties of the compounds are illustrated by the following examples:

EXAMPLE 1

Preparation of 1-Hydroxy-2-alkyl (or aryl) imidazoles

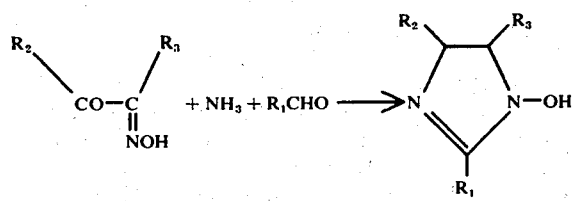

Equimolar amounts of aldehyde and the dione monoxime in the minimum volume of ethanol (95%) or dioxan were treated at room temperature with aqueous ammonia (d, 0.88: 80 ml/mole of dione monoxime) when an exotherm was usually noted. The temperature was not allowed to rise above 60°C and the reaction mixture was stirred at room temperature over-night and left standing for 24 hr. The solvent was distilled off in vacuo and the gummy residue was dissolved in the minimum volume of acetone and diluted with ether. Vigorous stirring was continued for several hours before collecting either solid or liquid product which had separated.

Products crystallized from acetone-ether analyzed for the anhydrous imidazoles. By crystallization from aqueous ethanol, monohydrates of these materials were obtained. These reverted to the anhydrous products on crystallization from acetone-ether. Both anhydrous imidazoles and hydrates could be used equally satisfactorily to prepare the derived carbamates.

Compounds prepared by this method include

| | | m.pt., °C |
|---|---|---|
| a) | 2,4,5-Trimethyl-1-hydroxyimidazole | 133–4 |
| b) | 4,5-Dimethyl-2-ethyl-1-hydroxyimidazole | 84–86 |
| c) | 4,5-Dimethyl-1-hydroxy-2-n-propylimidazole | 86–87 |
| d) | 4,5-Dimethyl-1-hydroxy-2-isopropylimidazole | 134–5 |
| e) | 4,5-Dimethyl-2-n-butyl-1-hydroxyimidazole; | 58–9 |
| f) | 4,5-Dimethyl-1-hydroxy-2-isobutylimidazole | * |
| g) | 4,5-Dimethyl-1-hydroxy-2-phenylimidazole | 115 |
| h) | 4,5-Dimethyl-2-benzyl-1-hydroxyimidazole; | 153–9 |
| i) | 4,5-Dimethyl-1-hydroxy-2-nitrophenylimidazole | 241–3 |
| j) | 4,5-Dimethyl-1-hydroxy-2-(4-isopropyl phenyl)imidazole. | 97–8 |
| k) | 4,5-Dimethyl-2-furyl-1-hydroxyimidazole | 166–8 |
| l) | 4,5-Diphenyl-1-hydroxy-2-isopropylimidazole | 241–3 |
| m) | 4,5-Diphenyl-1-hydroxy-2-isobutylimidazole | 228–230 |
| n) | 2,4,5-Triphenyl-1-hydroxyimidazole | 229–230 |
| o) | 4,5-Dimethyl-1-hydroxy-2-(4'-fluorophenyl) imidazole | 126–127 |
| p) | 4,5-Dimethyl-1-hydroxy-2-(4'hydroxy-3'-methoxyphenyl)imidazole. | 250 |
| q) | 4,5-Dimethyl-1-hydroxy-2-(3',4'-methylenedioxyphenyl)imidazole | 143 |
| r) | 4,5-Dimethyl-1-hydroxy-2-(3',4'-dichlorophenyl)-imidazole | 191–192 |
| s) | 4-Methyl-5-ethyl-1-hydroxy-2-n-propyl-imidazole | * |
| t) | 4-Methyl-5-ethyl-1-hydroxy-2-isopropyl-imidazole | * |
| u) | 4-Ethyl-5-methyl-1-hydroxy-2-n-propyl-imidazole | * |
| v) | 4-Ethyl-5-methyl-1-hydroxy-2-isopropyl-imidazole | * |
| w) | 4-Methyl-5-isopropyl-1-hydroxy-2-n-propyl-imidazole | * |
| x) | 4-Methyl-2,5-di-isopropyl-1-hydroxyimidazole | * |

* indicates that the oily compound was isolated and was purified by chromatography. Structure confirmed by IR, NMR spectra.

EXAMPLE 2

Preparation of 1-Hydroxy-2-alkyl-4-methyl-5-carbalkoxyimidazoles:

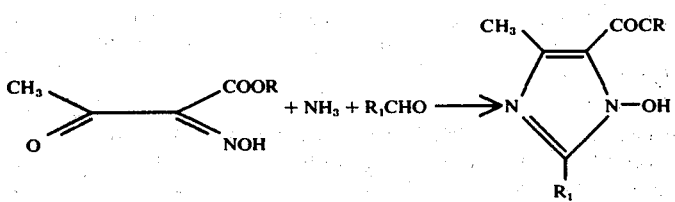

Equimolar amounts of aldehyde and α-isonitroso alkyl acetoacetate were suspended in dioxan and left stirring for 0.5 hr. To the resulting solution aqueous ammonia (d,0.88; 80 ml/mole of isonitroso ester) was added dropwise over 10–15 minutes. The reaction was then left stirring at room temperature for 72 hours. The resulting solid was filtered off and recrystallised from dioxan.

Compounds prepared by this method include:

| | | m.pt°C |
|---|---|---|
| a) | 1-Hydroxy-2-ethyl-4-methyl-5-carbethoxy-imidazole | 110 |
| b) | 1-Hydroxy-2-n-propyl-4-methyl-5-carbethoxy-imidazole | 101 |
| c) | 1-Hydroxy-2-iso-propyl-4-methyl-5-carbethoxy-imidazole | 148 |
| d) | 1-Hydroxy-2-n-propyl-4-methyl-5-carbomethoxy-imidazole | * |
| e) | 1-Hydroxy-2-iso-propyl-4-methyl-5-carbomethoxyimidazole | * |

* indicates that the compound was purified by chromatography and the structure confirmed by i.r. and n.m.r. spectra and g.l.c. and t.l.c. properties.

EXAMPLE 2

Preparation of 1-Hydroxy-3-alkyl (or aryl)-imidazole-3-oxides $$\underset{\substack{|\\NOH}}{R_2\diagdown\;\;\;/R_3\\CO-C}\quad\longrightarrow\quad\text{[imidazole N-oxide structure with } R_2, R_3, R_1, \bar{O}-N+, N-OH\text{]}$$

$$\underset{\substack{|\\R_1}}{\overset{+}{C}H=NOH}$$

A mixture of equimolar quantities of alkyl or aryl aldoxime and dione monoxime was warmed to obtain a homogeneous solution. After standing at room-temperature for 2 days, the mixture was heated on a steam-bath for 6 hr., kept overnight, and then diluted with ether. The solid separated, was removed by filtration and recrystallised from ethanol.

Compounds prepared by this method include:

| | | m.pt°C |
|---|---|---|
| a) | 4-Methyl-5-ethyl-1-hydroxy-2-n-propylimidazole-3-oxide. | 140 |
| b) | 4-Methyl-5-ethyl-1-hydroxy-2-isopropylimidazole-3-oxide. | 186 |
| c) | 4-Methyl-2,5-di-isopropyl-1-hydroxyimidazole-3-oxide. | 199 |
| d) | 4-Methyl-5-ethyl-1-hydroxy-2-phenylimidazole-3-oxide. | 174 |
| e) | 4,5-Dimethyl-1-hydroxy-2-methylimidazole-3-oxide* | 189–190 |
| f) | 4,5-Dimethyl-1-hydroxy-2-ethylimidazole-3 oxide* | 195 |
| g) | 4,5-Dimethyl-1-hydroxy-2-n-propylimidazole-3-oxide | 187–9 |
| h) | 4,5-Dimethyl-1-hydroxy-2-isopropylimidazole 3-oxide | 159–160 |
| i) | 4,5-Dimethyl-1-hydroxy-2-n-butylimidazole-3-oxide | 127–8 |
| j) | 4,5-Dimethyl-1-hydroxy-2-isobutylimidazole 3-oxide | 170–1 |
| k) | 4,5-Dimethyl-1-hydroxy-2-n-pentylimidazole-3-oxide | 132–133 |
| l) | 4,5-Dimethyl-1-hydroxy-2-nonylimidazole-3-oxide | 101–2 |
| m) | 4,5-Dimethyl-1-hydroxy-2-phenylimidazole-3-oxide* | 218–220 |

*These compounds have been previously described by J.B. Wright in J. Org. Chem., 1620(1964).

EXAMPLE 4

Preparation of 4,5-Dimethyl-1-hydroxy-2-n-propylimidazole-3-oxide

A mixture of butyraldoxime (8.7 g., 0.1 mole) and diacetyl monoxime (10.1 g., 0.1 mole) was warmed to obtain a homogeneous solution. After standing for 2 days at room-temperature, the mixture was heated on the steam-bath for 3 hr., and then diluted with ether (500 ml), the tan solid separated was removed by filtration (16.7 g.) and recrystallised from ethanol (95%) having a melting point 174°–175°C

EXAMPLE 5

General method for preparation of ketone monoxime

Into a vigorously stirred solution of ketone in diethyl ether was passed HCl gas at a rate of 8–10 bubbles per minute. After ten minutes, amyl nitrite was added dropwise over an hour at such a rate as to maintain gentle refluxing. When the addition was over, HCl gas was bubbled in for an additional half hour and the reaction mixture was left overnight at room-temperature. The ethereal layer was washed with 5% NaOH and finally poured onto ice/HCl with stirring. The precipitate which formed was filtered, washed and dried in a desiccator.

Typical of the products prepared were isonitrosoisobutyl methyl ketone, m.p. 70° and isonitroso ethyl isopropyl ketone, m.p. 90° and isonitroso methyl n-propyl ketone, m.p. 57°.

EXAMPLE 6

General method for preparation of α-isonitroso alkyl aceto-acetate.

Alkyl acetoacetate and glacial acetic acid were mixed and cooled to 5°–7°C. An aqueous sodium nitrite was added dropwise with stirring over 0.5 hr. The resulting solution was kept at 5°–7°C for further 0.5 hr., and then allowed to warm up to room temperature over 4 hrs. The mixture was poured onto ice and water and extracted with chloroform. The extract was washed with water, dried and the solvent evaporated to yield a pale yellow oil which was then carefully distilled*.

*The distillation of isonitroso esters must be carried out carefully within 1-3 hours after isolation of the crude product. The distillation after leaving the crude oil overnight resulted in violent explosion.

Typical of the products prepared were:

a. α-Isonitroso ethyl acetoacetate, b.p. 124°/1mm or 108°/0.3 mm.

b. α-Isonitroso methyl acetoacetate, b.p. 112°–114°/0.4-0.5 mm.

EXAMPLE 7

Preparation of 1-N-alkyl (or aryl) carbamoyloxy-2-alkyl (or aryl)-imidazoles

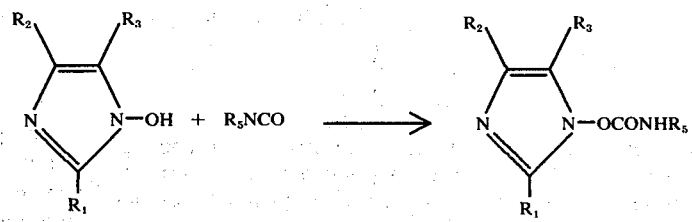

To a stirred mixture of 0.01 mole of the appropriate N-hydroxy-imidazole in 60 ml of dry acetone at room temperature was added slowly 0.012 mole of alkyl (or aryl) isocyanate in 10 ml of dry acetone. After the addition was complete, the flask was stoppered and stirring was continued for ca.20 hours. The solvent was evaporated at reduced pressure and the crude product purified by recrystallisation, preferably from ether.

Compounds prepared by this method include

|    |                                                            | m pt °C. |
|----|------------------------------------------------------------|----------|
| a) | 4,5-Dimethyl-2-ethylimidazole-1-methylcarbamate.           | 94–5     |
| b) | 4,5-Dimethyl-2-isopropylimidazole-1-methylcarbamate.       | 101–2    |
| c) | 4,5-Dimethyl-2-isobutylimidazole-1-methylcarbamate.        | 40       |
| d) | 4,5-Dimethyl-2-phenylimidazole-1-methylcarbamate.          | 130–2    |
| e) | 4,5-Dimethyl-2-isopropylphenylimidazole-1-methylcarbamate. | 101–2    |
| f) | 4,5-Dimethyl-2-(2-furyl)imidazole-1-methylcarbamate.       | 103–4    |
| g) | 4,5-Dimethyl-2-ethylimidazole-1-ethylcarbamate.            | 99–100   |
| h) | 4,5-Dimethyl-2-phenylimidazole-1-ethylcarbamate            | 128–130  |
| i) | 4,5-Dimethyl-2-phenylimidazole-1-allylcarbamate.           | 112–3    |
| j) | 4,5-Dimethyl-2-(2-furyl)imidazole-1-phenylcarbamate.       | 145–6    |

EXAMPLE 8

Preparation of 1-N, N-dimethyl (or diethyl)-carbamoyloxy-2-alkyl (or aryl-imidazoles).

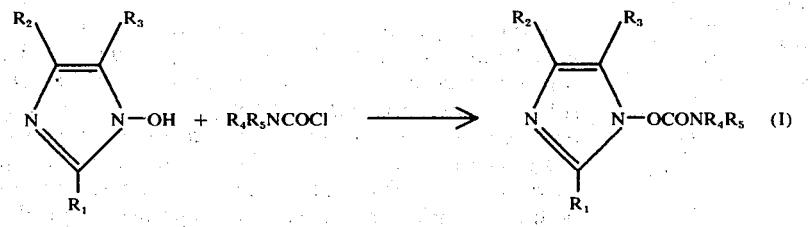

Sodium metal (0.1 mole) was dissolved in the minimum volume absolute ethanol or methanol and then stripped to dryness in vacuo. A solution of 0.1 mole of the N-hydroximidazole in dry benzene was added and the mixture heated to reflux for 0.5 hr., during which time a sodium salt separated. The di-alkylcarbamoyl chloride (0.1 mole) was added dropwise and refluxing continued for several hours (4–20 hrs). Upon cooling, inorganic salt was filtered out and the solvent was removed under vacuum when an oily product was obtained. This was further purified either by vacuum distillation or by column chromatography on silica gel.

Compounds prepared by this method include:

|    |                                                          | B.p. °C at mm pressure |
|----|----------------------------------------------------------|------------------------|
| a) | 4,5-Dimethyl-2-methylimidazole-1-dimethylcarbamate.      | 133–4°/0.75 mm         |
| b) | 4,5-Dimethyl-2-ethylimidazole-1-dimethylcarbamate.       | 123–4°/0.45 mm         |
| c) | 4,5-Dimethyl-2-n-propylimidazole-1-dimethylcarbamate     | 134–6°/0.15 mm         |
| d) | 4,5-Dimethyl-2-isopropylimidazole-1-dimethylcarbamate    | 112–4°/0.15 mm         |
| e) | 4,5-Dimethyl-2-n-butylimidazole-1-dimethylcarbamate      | 130–2°/0.25 mm         |
| f) | 4,5-Dimethyl-2-isobutylimidazole-1-dimethylcarbamate.    | 140°/0.8 mm            |
| g) | 4,5-Dimethyl-2-phenylimidazole-* dimethylcarbamate       |                        |
| h) | 4,5-Dimethyl-2-benzylimidazole-1-* dimethylcarbamate.    |                        |
| i) | 4,5-Dimethyl-2-isopropylimidazole-1-diethylcarbamate.    | 130–131°/0.3 mm        |
| j) | 4,5-Dimethyl-2-isobutylimidazole-1-diethylcarbamate.     | 138–140°/0.5 mm        |
| k) | 4-Methyl-2,5-diethyl imidazole-1-dimethylcarbamate.      | 120–122°/0.3–0.4       |
| l) | 4-Methyl-5-ethyl-2-n-propylimidazole-1-dimethylcarbamate.| 125–128°/0.6 mm        |
| m) | 4-Methyl-5-ethyl-2-isopropylimidazole-1-dimethylcarbamate.| 120–124°/0.4 mm       |
| n) | 4-Methyl-5-isopropyl-2-n-propylimidazole-dimethylcarbamate. | 122°/0.4 mm.        |
| o) | 4-Methyl-2,5-di-isopropylimidazole-1-dimethylcarbamate.  | 125°/0.4 mm.           |
| p) | 4-Ethyl-5-methyl-2-n-propylimidazole-1-dimethylcarbamate.| 146°/1.2 mm            |
| q) | 4-Ethyl-5-methyl-2-isopropylimidazole-1-dimethylcarbamate.| 127–128°/1 mm         |

*indicates that the oily compound was isolated and was purified by chromatography. Structure confirmed by IR, NMR spectra.

EXAMPLE 9

Preparation of 1-N,N-dimethylcarbamoyloxy-2-alkyl-4-methyl-5-carbealkoxyimidazole.

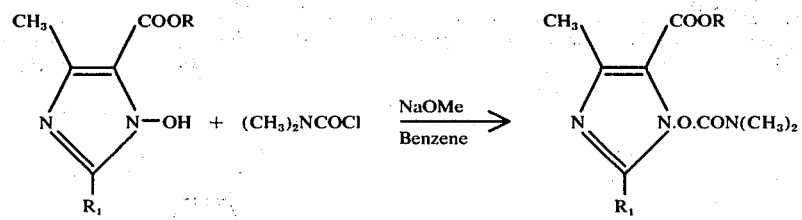

To the stirred suspension of dry sodium methoxide (0.011 mole) and N-hydroxyimidazole ester (0.01 mole) in dry benzene (50 ml), the dimethylcarbamoylchloride (0.11 mole) was added dropwise and stirring continued for 24 hrs at room temperature. The reaction was left standing for further 72 hrs. The inorganic salt was filtered out and the solvent was removed under vacuum when an oily product was isolated. It was further purified by vacuum distillation. Compounds were fully identified by IR, NMR spectra and C,H,N analysis figures. Compounds prepared by this method include:

a. 1-N,N-dimethylcarbamoyloxy-2-isopropyl-4-methyl-5-carbethoxy imidazole b.p: 153°/1.3mm b. 1-N,N-dimethylcarbamoyloxy-2-n-propyl-4-methyl-5-carbmethoxy-imidazole b.p: 136°/0.8mm c. 1-N,N-dimethylcarbamoyloxy-2-isopropyl-4-methyl-5-carbmethoxy imidazole b.p: 120°/1mm

EXAMPLE 10

Preparation of 1-N,N-dimethylcarbamoyloxy-4,5-dimethyl-2-n-propylimidazole-3-oxide To freshly prepared dry sodium methoxide (from 350 mg of Na in 10 ml of methanol) was added a solution of 2.6 g of 4,5-dimethyl-1-hydroxy-2-n-propylimidazole-2-oxide in dry benzene (80 ml) and the mixture stirred at room temperature for 30 mins. 1.8g of dimethylcarbamoyl chloride was added and refluxing continued for 48 hr. After filtering, to remove inorganic material, the solvent was stripped in vacuo when a reddish oil (3.1 g) was isolated. This was purified by chromatography on a silica gel column, using chloroform.

The compound was fully indentified by its i.r. and n.m.r. spectra and C,H,N analysis figures.

EXAMPLE 11

1-N,N-Dimethylcarbamoyloxy-4-methyl-5-ethyl-2-isopropylimidazole-3-oxide was prepared in a similar manner to that described in Example 10.

EXAMPLE 12: Insecticidal activity

Test 1.

Adult *Drosophila melanogaster* were tested by contact with plates coated with known concentrations of test compounds applied in acetone solution, together with suitable surfactants, the acetone being evaporated to leave known amounts of test compound per unit area. The proportion of insects dead after 24 hours was recorded.

Test 2

1 inch discs of leaf tissue were excised from broadbean plants, immersed in 5% acetone/water solutions of known concentrations. The discs were then placed in a perspex frame and supplied with water by wicks. Nymphal forms of *Aphis fabae* were then placed on the discs and suitably restrained. The proportion of insects dead after 48 hours was recorded.

TABLE 1

| Compound | Test 1 *Drosophila* adults $LD_{50}(mg/cm^2)$ | Test 2 *Aphis fabae* nymphs $LD_{50}$(ppm in dip solution) |
|---|---|---|
| 4,5-Dimethyl-2-isopropyl-imidazole-1-dimethylcarbamate | 1.2 | 50 |
| 4,5-Dimethyl-2-n-propyl-imidazole-1-dimethylcarbamate | 0.7 | 20 |
| 4,5-Dimethyl-2-n-propyl-imidazole-1-dimethylcarbamate 3-oxide. | 0.9 | 10–30 |
| 4,5-Dimethyl-2-benzyl-1-hydroxyimidazole. | not tested. | 200 |
| 4,5-Dimethyl-1-hydroxy-2-n-propylimidazole | not tested | 90 |
| 2-isopropyl-4-methyl-5-carbmethoxyimidazole-1-dimethylcarbamate. | 5.0 | 150 |
| 2-n-propyl-4-methyl-5-carbmethoxyimidazole-1-dimethyl carbamate. | 2.5 | 350 |
| 2-isopropyl-4-methyl-5-carbmethoxyimidazole-1-dimethyl carbamate. | 1.2 | 100 |

EXAMPLE 13

Test 3

The main tap root was immersed in 5% acetone/water solution of the test material at 100, 50 and 25 ppm. for over 24 hours, the subsidiary roots being maintained in water. At the end of that period the test material was removed and nymphal aphids placed on the leaves. The proportion of insects dead after 48 hours was recorded.

Test 4

One leaf of a bean plant growing in soil was immersed in a 5% acetone/water solution of the test material for 24 hours. At the end of this time the test material was removed, the leaf was bound with muslin and nymphal aphids placed on the other leaves. The proportion of insects dead after 48 hours was recorded.

TABLE 2

| Compound | Mortalities (%) Test 3 by root absorption. 100 ppm | 50 ppm | 25 ppm | Test 4 by leaf absorption 100 ppm | 50 ppm |
|---|---|---|---|---|---|
| 4,5-Dimethyl-2-isopropyl-imidazole-1-dimethylcarbamate. | 78% | 54% | — | 76% | 30% |
| 4,5-Dimethyl-2-n-propyl-imidazole-1-dimethylcarbamate | 94% | 90% | 73% | 74% | 35% |
| 4,5-Dimethyl-2-n-propyl-imidazole-1-dimethylcarbamate 3-oxide. | 30% | — | — | 52% | — |

EXAMPLE 14

The insecticidal compositions may be in the form of seed dressings wherein the active ingredient is mixed with an inert solid, such as Fullers Earth, talc, kaolin or bentonite. The said dressings may be applied to seeds, for example broad bean seeds, at a rate of between 0.1% and 33% by weight of the seed of active ingredient, and the young plants eventually obtained from the dressed seed are protected against infestation by *Aphis fabae* for a period of at least 2 weeks.

EXAMPLE 15

Translaminar properties of 4,5-dimethyl-2-n-propylimidazole-1-dimethylcarbamate.

Leaf discs are taken, the upper surface is carefully treated with 5% acetone/water solution of the material.

The disc is then dried and placed, upper surface down, in a perspex frame, and the test then proceeds as in Test 2, in Example 8 above. The proportion of insects dead after 48 hours was recorded and the results are shown in table 3.

TABLE 3

| | Mortalities (%) of *Aphis fabae* nymphs by translaminar effect. | | | |
|---|---|---|---|---|
| | 200 ppm. | 100 ppm | 50 ppm | 25 ppm |
| Compound (ii) | 60% | 52% | 47% | 39% |

We claim:

1. An insecticidal composition comprising an insecticidally effective amount of a compound of the formula:

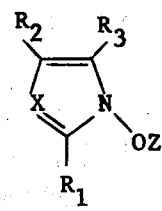

wherein $R_1$ is hydrogen or alkyl of 1 to 6 carbon atoms, $R_2$ and
$R_3$ are the same or different and each is hydrogen or alkyl of 1 to 6 carbon atoms,
X is N or N → O, and
Z is $CONR_4R_5$ wherein $R_4$ is hydrogen, alkyl of 1 to 6 carbon atoms, benzyl or phenyl and $R_5$ is hydrogen, alkyl of 1 to 6 carbon atoms or phenyl, in combination with a suitable carrier.

2. A composition according to claim 1, wherein $R_1$ is alkyl of 1 to 6 carbon atoms and $R_2$ and $R_3$ are the same or different and each is alkyl of 1 to 6 carbon atoms.

3. A composition according to claim 2, wherein $R_4$ is hydrogen or alkyl of 1 to 6 carbon atoms and $R_5$ is alkyl of 1 to 6 carbon atoms.

4. A composition according to claim 1, wherein $R_1$ is methyl, ethyl, n-propyl, isopropyl, n-butyl, isobutyl, sec.-butyl or t.-butyl, $R_2$ and $R_3$ are the same or different and each is hydrogen, methyl, ethyl, propyl or butyl, $R_4$ is hydrogen, methyl, ethyl, propyl or butyl and $R_5$ is methyl, ethyl, propyl or butyl.

5. A composition according to claim 2, wherein $R_4$ and $R_5$ are each methyl or ethyl.

6. A composition according to claim 2, wherein Z is $CO-N(CH_3)_2$.

7. A composition of claim 1, wherein the insecticidal compound is in the form of the sulphate, nitrate, phosphate, hydrohalide, acetate or formate.

8. A composition according to claim 1, wherein the compound is 4,5-dimethyl-2-isopropylimidazole-1-methylcarbamate.

9. A composition according to claim 1, wherein the compound is 4,5-dimethyl-2-isobutylimidazole-1-methylcarbamate.

10. A composition according to claim 1, wherein the compound is 4,5-dimethyl-2-ethylimidazole-1-ethylcarbamate.

11. A composition according to claim 1, wherein the compound is 4,5-dimethyl-2-methylimidazole-1-dimethylcarbamate.

12. A composition according to claim 1, wherein the compound is 4,5-dimethyl-2-ethylimidazole-1-dimethylcarbamate.

13. A composition according to claim 1, wherein the compound is 4,5-dimethyl-2-n-propylimidazole-1-dimethylcarbamate.

14. A composition according to claim 1, wherein the compound is 4,5-dimethyl-2-isopropylimidazole-1-dimethylcarbamate.

15. A composition according to claim 1, wherein the compound is 4,5-dimethyl-2-n-butylimidazole-1-dimethylcarbamate.

16. A composition according to claim 1, wherein the compound is 4,5-dimethyl-2-isobutylimidazole-1-dimethylcarbamate.

17. A composition according to claim 1, wherein the compound is 4,5-dimethyl-2-isopropylimidazole-1-diethylcarbamate.

18. A composition according to claim 1, wherein the compound is 4,5-dimethyl-2-isobutylimidazole-1-diethylcarbamate.

19. A composition according to claim 1, wherein the compound is 4-methyl-2,5-diethylimidazole-1-dimethylcarbamate.

20. A composition according to claim 1, wherein the compound is 4-methyl-5-ethyl-2-n-propylimidazole-1-dimethylcarbamate.

21. A composition according to claim 1, wherein the compound is 4-methyl-5-ethyl-2-isopropylimidazole-1-dimethylcarbamate.

22. A composition according to claim 1, wherein the compound is 4-methyl-5-isopropyl-2-n-propylimidazole-1-dimethylcarbamate.

23. A composition according to claim 1, wherein the compound is 4-methyl-2,5-di-isopropylimidazole-1-dimethylcarbamate.

24. A composition according to claim 1, wherein the compound is 4-ethyl-5-methyl-2-n-propylimidazole-1-dimethylcarbamate.

25. A composition according to claim 1, wherein the compound is 4-ethyl-5-methyl-2-isopropylimidazole-1-dimethylcarbamate.

26. A method for the control of insects which comprises applying to the insect or its habitat an insecticidally effective amount of a composition of claim 1.

27. A method for the control of insects which comprises applying to the insect or its habitat an insecticidally effective amount of a composition of claim 6.

28. A method for the control of insects which comprises applying to the insect or its habitat an insecticidally effective amount of a composition of claim 13.

29. A method for the control of insects which comprises applying to the insect of its habitat an insecticidally effective amount of a composition of claim 7.

* * * * *